United States Patent [19]

Zhao

[11] Patent Number: 5,464,620
[45] Date of Patent: Nov. 7, 1995

[54] PHARMACEUTICAL COMPOSITION FOR TREATING GASTROINTESTINAL DISEASE

[76] Inventor: Xinxian Zhao, Shenzhen, China

[21] Appl. No.: 273,231

[22] Filed: Jul. 1, 1994

[51] Int. Cl.⁶ .................................................. A61K 35/78
[52] U.S. Cl. .................... 424/195.1; 514/925; 514/926; 514/927
[58] Field of Search .................. 424/195.1; 514/926, 514/927, 925

[56] References Cited

U.S. PATENT DOCUMENTS 4,608,258  8/1986  Yamonaka ............................ 424/198.1
5,324,516  6/1994  Rak et al. ............................ 424/195.1

*Primary Examiner*—John W. Rollins

[57] ABSTRACT

The invention relates to a pharmaceutical composition, which is useful in the treatment of gastrointestinal disorders, especially gastric ulcer, duodenal ulcer and gastritis. The pharmaceutical composition is composed of Rhizoma coptidis extract, Radix scutellariae extract, and Radix astragali extract. Processes for producing these components are provided.

1 Claim, No Drawings

PHARMACEUTICAL COMPOSITION FOR TREATING GASTROINTESTINAL DISEASE

BACKGROUND OF THE INVENTION

The invention relates to a new herb's drug which is comprising of Rhizoma coptidis extract, Radix scutellariae extract, and Radix astragali extract. The new drug is useful for the treatment of gastrointestinal disease, especially gastric ulcer, duodenal ulcer and gastritis.

DESCRIPTION OF PRIOR ART

The pathogenesis of peptic ulcer disease is not completely understood. It is clear that gastric acid and pepsin secretion are necessary for the development of a peptic ulcer. However, factors relating to mucosal resistance to acid and pepsin are also important, particularly in gastric ulcer disease. Currently, drugs are available that have some effect on each of these factors. For example, antacids, $H_2$—receptor antagonists, anticholinergics, mucosal protective agents, pancreatic enzyme replacement products et. al were used for treatment gastrointestinal disease. Although peptic ulcers occur only in the presence of gastric acid, they are not necessarily related to an overproduction of acid, as is commonly assumed. Some people who produce low levels of acid develop ulcers, while there are others produce large amounts yet ulcer-free. A number of factors can effect ulcer. For example, stress and the use of nonsteroidal anti-inflammatory drugs like aspirin are the most frequently encountered. Cigarette smoking and alcohol use may exacerbate existing ulcers, but it has not been proved that they actually cause them. Also, contrary to popular belief, spicy foods do not appear to a cause. More important fact, which is relative to ulcer, is helicobacter pylori.

In fact, at recently some reports have been shown that Helicobacter Pylori is associated with gastritis, duodenal and gastric ulcers, non-ulcer dyspepsia and hypochlorhydria. Helicobacter pylori is susceptible to Rhizoma coptidis and Radix scutellariae. The minimal inhibitory concentration (MIC) of Radix scutellariae extract and its active ingredient baicalin against helicobacter pylori is 250 and 125 µg/ml, respectively.

Berberine has been clinically used in the treatment of duodenal and gastric ulcers, for example, 50 patients who have Helicobacter pylori positive peptic ulcer taken 300 mg berberine 4 times daily for 4 weeks, 70% of patients' ulcer healed, 50% of patient's Helicobacter pylori became negative.

Baicalin and baicalein are active ingredients of Radix scutellariae. They can inhibit leukotriene synthesis. It has been shown that patients with peptic ulcer and gastritis have high gastric leukotriene level. Leukotriene can contract capillary of gastric mucosal and decrease the gastric mucosal blood flow, therefore it is harmful to the ulcer healing. Astragalic polysaccharide, which extracted from Radix astragali, can protect gastric mucosa.

So far, no one drug has been succeed to inhibit helicobucter pylori, treat gastrointestinal ulcer and meanwhile, it is very save. The new herb's drug coves the al benefits of single herb's drug or its ingredient mentioned above. Also it decreases the side effects of single herb's drug.

DETAIL DESCRIPTION

The herb drug, according to the invention, has the following compositions:

| | |
|---|---|
| Rhizoma coptidis extract | 5–40% |
| Radix scutellariae extract | 5–40% |
| Radix astragali extract | 30–60% |

For the sake of convenience, herb drug comprising mixtures of above extracts will be referred to HDG. HDG, according to the invention, is effective in the treatment of gastrointestinal disorders, especially duodenal and gastric ulcer and gastritis.

HDG, according to the invention, may be formulated into capsules, tablets and granules in a conventional manner using one or more pharmaceutically acceptable carrier, excipients, binding agent (e.g. pregelatinised maize starch or hydroxy propyl methyl cellulose), Lubricant (e.g. magnesium stearate, talc or silica) and disintegrant (e.g. dry maize starch). Tablets may be coated by methods will known it the art.

The unit dose of HDG is composed of 300 mg extract of Rhizoma coptidis, 300 mg extract of Radix scutellariae and 400 mg extract of Radix astragali. The unit dose may be administered one to four times daily, preferable three times. Also the dosage is depending on the age and weight of the patients.

The following specific examples will provide detailed illustrations of methods of producing HDG according to the present invention and pharmaceutical dosage units containing HDG. These examples are not intended, however, to limit or restrict the scope of the invention in any way, and should not be construed as providing conditions, parameters, reagents, or starting materials which must be utilized exclusively in order to practice the present invention.

Example 1. Rhizoma Coptidis Extract 1 kg Rhizoma coptidis was extracted with 1% HCl at 80°C. for 1 hour three times. 10 L of 1% HCl was used each time. The extractive was combined, filtered and concentrated at 70° C. under vacuo, dried at 60° C. in vacuo, 200 g dry extract was resulted.

Example 2. Radix Scutellariae Extract 1 kg Radix scutellariae was extracted with water at 80° C. for 1 hour three times. Each time 10 L of water was used. The extractive was combined, filtered and concentrated to 5 L, HCl was added, washed the precipitated with water to PH 7. Dried at 60° C. under vacuo, 100 g dry extract was resulted.

Example 3. Radix Astragli Extract 1 kg Radix astragali was extracted with water at 80° C. for 1 hour three times. Each time 10 L of water was used. The extractive was combined, filtered and concentrated at 70° C. under vacuo, dried at 60° C. under vacuo. 200 g dry extract was resulted.

Example 4. Capsules

The extract of Rhizoma coptidis, Radix scutellariae and Radix astragali were screened through 400 micron mesh sieve, blended together, and granulated with pregelatinised starch paste, the wet mass was dried at 80° C. for 4–8 hours and milled. The granule was filled into hard gelatin capsule.

|  | mg/capsule |
| --- | --- |
| *Rhizoma coptidis* extract | 150 mg |
| *Radix scutellariae* extract | 150 mg |
| *Radix astragali* extract | 200 mg |
| Pregelatinised starch | q.s. |

Example 5. Tablets

|  | mg/tablet |
| --- | --- |
| *Rhizoma coptidis* extract | 150 mg |
| *Radix scutellariae* extract | 150 mg |
| *Radix astragali* extract | 200 mg |
| Maize starch | 100 mg |
| Talc | q.s. |

Example 6. Granules

|  | mg/granule |
| --- | --- |
| *Rhizoma coptidis* extract | 300 mg |
| *Radix scutellariae* extract | 300 mg |
| *Radix astragali* extract | 400 mg |
| Pregelatinised starch | 200 mg |
| Lactose | 300 mg |

The preparation of HDG is simple and can be accomplished by the extraction methods set forth above or any conventional methods for extracting the active principles from the plant tissues. The novelty of the present invention resides in the mixture of the active principles in the specified proportions to produce HDG and in the preparation of dosage units in pharmaceutically acceptable dosage form. The term "pharmaceutically acceptable dosage form" as used hereinabove includes any suitable vehicle for the administration of medications known in the pharmaceutical art, including, by way of example, capsules, tablets, syrups, elixirs, and solutions for parenteral injection with specified ranges of HDG concentration.

In addition, the present invention provides novel methods for treating a variety of gastrointestinal disease with one easily produced, safe herb's drug.

It will thus be shown that there are provided compositions and methods which achieve the various objects of the invention, and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

I claim:

1. A pharmaceutical composition for the treating of gastritis, duodenal and gastric ulcer comprising:

5–40 wt % of hydrochloric acid extract of Rhizoma coptidis;

5–40 wt % of water extract of Radix scutellariae; and

30–60 wt % of water extract of Radix astragali.

\* \* \* \* \*